United States Patent [19]
LaRocca

[11] Patent Number: 5,209,234
[45] Date of Patent: May 11, 1993

[54] APPARATUS FOR THE NON-INTRUSIVE FRAGMENTATION OF RENAL CALCULI, GALLSTONES OR THE LIKE

[75] Inventor: Aldo LaRocca, Revigliasco Torinese, Italy

[73] Assignee: Lara Consultants s.r.l., Italy

[21] Appl. No.: 827,870

[22] PCT Filed: Sep. 29, 1988

[86] PCT No.: PCT/IT88/00068
§ 371 Date: Mar. 23, 1990
§ 102(e) Date: Mar. 23, 1990

[87] PCT Pub. No.: WO89/02724
PCT Pub. Date: Apr. 6, 1989

Related U.S. Application Data

[63] Continuation of Ser. No. 490,575, Mar. 23, 1990, abandoned.

[30] Foreign Application Priority Data

Oct. 2, 1987 [IT] Italy ............................ 48443 A/87

[51] Int. Cl.5 ............................................ A61B 17/22
[52] U.S. Cl. .............................. 128/660.03; 128/24 FL
[58] Field of Search ........ 128/24 AA, 24 FL, 660.03; 606/128

[56] References Cited

U.S. PATENT DOCUMENTS 4,315,514 2/1982 Drewes et al. ................. 128/24 AA
4,803,995 2/1989 Ishida et al. ..................... 128/660.03

Primary Examiner—Ruth S. Smith
Attorney, Agent, or Firm—Wegner, Cantor, Mueller & Player

[57] ABSTRACT

The apparatus for the non-intrusive fragmentation of renal calculi, gallstones or the like according to the invention comprises at least one ultrasonic receiver-transmitter head (12) focused on the renal calculus (11), gallstone or the like to be disintegrated, a head (12) being associated with a low-power variable frequency transmitter (16) and with a receiver (18) to perform a spectral analysis of the characteristic resonance frequencies of the renal calculus (11), gallstone or the like to be disintegrated, and a controller (Tx1, OSC1) to cause a transmitter (16) to emit relatively high-power energy peaks at the characteristic resonance frequencies of the renal calculus (11), gallstone or the like to promote its disintegration.

5 Claims, 5 Drawing Sheets

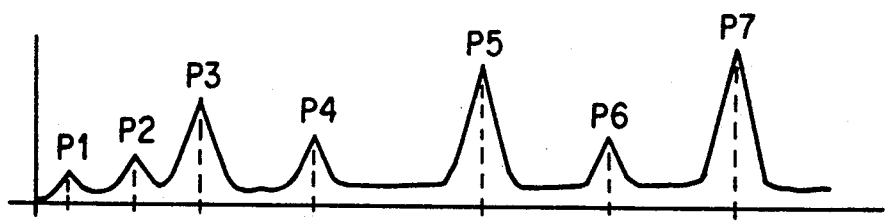
FIG. 6a
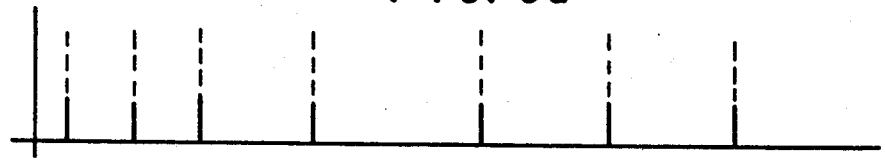
FIG. 6b
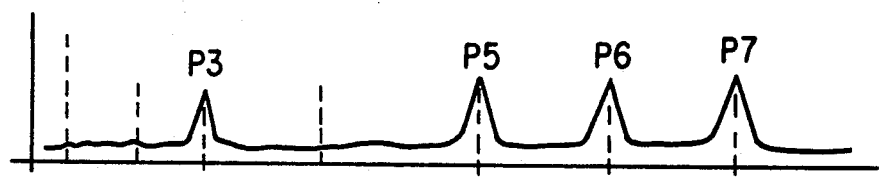
FIG. 6c
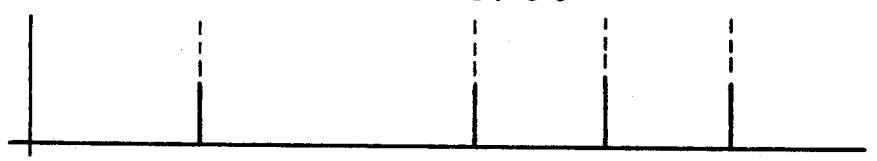
FIG. 6d
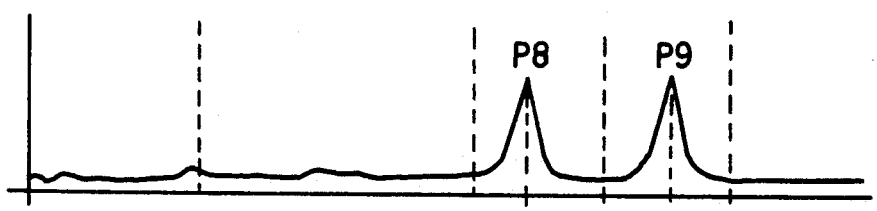
FIG. 6e
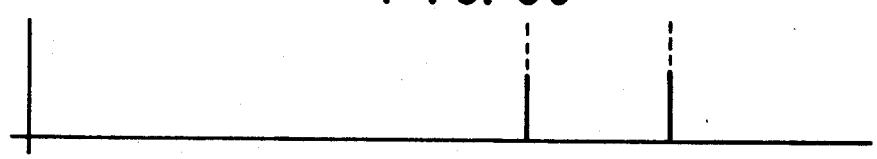
FIG. 6f
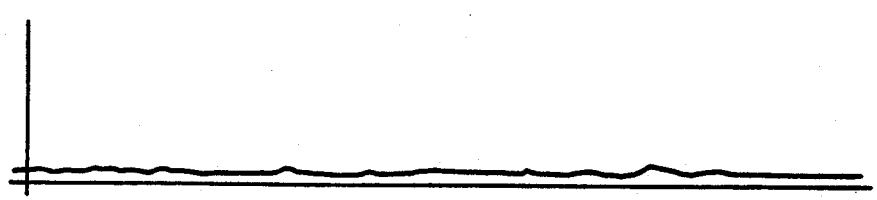
FIG. 6g → FREQUENCY

APPARATUS FOR THE NON-INTRUSIVE FRAGMENTATION OF RENAL CALCULI, GALLSTONES OR THE LIKE

This application is a continuation of U.S. application Ser. No. 07/490,575, filed Mar. 23, 1990, now abandoned.

This invention relates to an apparatus for the non-intrusive fragmentation of renal calculi, gallstones or the like.

It is well known that the conventional method of removing renal calculi, gallstones or the like is by surgery.

Recently however, much effort has been dedicated to the search for non-sanguinary and in particular non-intrusive techniques for fragmenting renal calculi in such a manner as to disintegrate their structure and break them down into particles which can be eliminated naturally without inconveniencing the patient.

In this respect, the "sanguinary" method is of known inconvenience in terms of hospitalization and its associated cost, plus the inevitable surgical shock. The latter in particular can be intolerable to debilitated, elderly, diabetic and other patients, so making the operation impraticable because of the increased risk factor. This and the other said inconveniences should in all cases be avoided, and this has lead to the search for other techniques. Up to a short time ago these were of intrusive character, using special active and/or passive catheters because of the traumatic side effects.

An intermediate method between the completely surgical and the catheter methods has been used in recent years. In this method, a metal probe is brought into contact with the calculus by surgical incision and then transmits to it an ultrasonic mechanical action by the effect of an ultrasonic exciter to which said probe is connected. The technique has proved effective in the fragmentation of and their succesive "natural" elimination with adjuvant clinical intervention. However, although substantially reduced, the inconvenience of even a minor surgical operation still exists.

The non-sanguinary non-intrusive techniques used up to the present time are based on the use of a field or beam of mechanical energy waves generated outside the patient's body, to interact with the constituent concretions of the calculus and cause its fragmentation by "brute force".

The mechanical energy used, which is in the form of ultrasonic or shock waves generated external to the patient, is liberated during the process of their absorption by him, and preferentially by the calculus itself (this selectivity being the distinguishing merit of these techniques) to lead to disintegration of the constituent polycrystalline concretions of the renal calculus.

The ultrasonic techniques of the known art use so-called "brute force", with peak powers reaching 100 kW. In this context, the term "brute force" is used in relation to known techniques because the apparatus concerned relies wholly on the power density applied to the constituent crystalline concretion of the renal calculus, whether it is of semi-fine or fine structure and whatever its size. This approach, especially in the case of shock waves, carries the danger of damaging other biological structures besides the renal calculi themselves, and has numerous disadvantages such as the need to totally anesthetize the patient, the need to completely immerse the bound patient in water or the like, etc.

For example, EP-A-0 133 665 cites as known art certain methods using ultrasonic waves which reach a peak power of 100 kW. The apparatus of that invention, which comprises a spark shock wave generator with wave guides and a focusing lens, certainly applies "brute force".

EP-A-0 133 946 describes a structure for disintegrating renal calculi by means of a plurality of shock wave generators which converge at a common focal point. The technique is again a shock wave and therefore "brute force" technique.

EP-A-0 162 959 describes the generation of shock waves for disintegrating renal calculi by means of an electromechanical structure comprising a pulse-energised electromagnetic coil. "Brute force" is again applied in this case.

EP-A-0 167 670 describes a system for generating shock waves by interaction between electromagnetic microwaves and the structures to be demolished. Fragmentation is thus again by "brute force".

The most recent known art, exemplified by the aforesaid patent references, shows that research has up to now been based on the use of high-density power with extremely wide and irregular spectral distribution (shock waves) to obtain mechanical fragmentation of the constituent concretions of calculi. In addition, it should be noted that elastic waves within a relatively wide spurious spectrum cannot give correct focusing of the transmitted energy on the calculi to be demolished, with the result that only part of the ultrasonic energy transmitted to the patient is effectively used in demolishing the calculi. The remainder is dispersed and can act negatively on those structures which fortuitously absorb energy.

The result is a situation similar to that which prevailed in the use of light energy, including for therapeutic purposes, before the large-scale introduction of coherent light (laser), or in spark radio transmission before continuous wave.

In this respect, it is a well known fact of physics that in the case of oscillation (electrical, mechanical), monochromaticity and phase coherence of the oscillation allows accurate focusing and aiming, and thus the concentration of the available energy at a well determined point in space. It is also a well known fact that in the mechanical field (such as disintegration of renal calculi, gallstones or the like) maximum energy transfer between the elastic wave source and a structure to be oscillated is obtained under conditions of resonance on one or more of the resonance modes of the structure. In this respect it is known that in mechanical structures subjected to dynamic stresses, steps are taken to prevent oscillation and/or vibrations which could assume destructive amplitude.

In contrast to the known art the apparatus of the present invention uses ultrasonic waves having a wavelength falling within a very narrow band such that they can be precisely focused by wave guides, mirrors or acoustic lenses.

This is quite different from the system developed at Munich University by Dornier, which does not use ultrasonic waves but instead uses the brute force of explosions (shock waves) caused by striking intense electric sparks at the focal point of two large (30–40 cm) parabolic reflectors immersed in a water-filled tank in which the bound and anesthetized patient is also immersed (details of the Dornier system are given inter alia in the Italian magazine 'TRENTATRE'—Dimensione salute, May 1986, page 68 onwards).

In this, each spark generates a steam pulse equivalent to an explosion, the shock wave of which propagates within the incompressible medium formed by the water, to strike a not indifferent blow to the patient's abdomen.

As stated, two such reflectors and shock wave generators are immersed in the tank. The reflectors focus the shock waves onto the calculus so that on releasing the waves in synchronism they break down the calculus using their brute force.

As these waves have a rather wide and poorly defined spectral distribution and equivalent wavelength, their focusing is fairly imprecise and consequently their action synchronism is poor, these being aspects on which the efficiency of the system entirely depends. This perhaps explains the difficulties sometimes encountered in operating it correctly.

According to the invention, there is provided an apparatus for the non-intrusive fragmentation of renal calculi by ultrasonic oscillations which are focused on the renal calculus to be disintegrated, characterised by comprising at least one receiver-transmitter head for ultrasonic waves which are focused on the renal calculus to be disintegrated, each of said heads comprising variable frequency transmitter means for the generation of ultrasonic oscillations having wavelengths falling within a very narrow band and receiver means, said apparatus further comprising control means to effect a frequency sweep at low power, and means connected to the receiver means to perform a spectral analysis of the characteristic resonance frequencies of the calculus to be disintegrated, whereupon said transmitter means is caused to emit, at the characteristic resonance frequencies of said calculus, relatively high-power energy pulses possessing the minimum energy adequate to promote its disintegration.

The principle of operation of the apparatus according to the invention is as follows.

Each of the two focusing heads contains a sensor which picks up the reflection of its signal from an obstacle, in this case the calculus, and having determined the position of this latter by direct X-ray analysis and/or by ascending or descending pyeloscopy etc., the ultrasonic beam is directed and focused onto this position so as to obtain maximum reflected signal response for a given area of covering (partial or total) of the calculus. The percentage of area is chosen according to the calculus type and size and the optimised program for applying the power and energy intensity necessary for its fragmentation.

The position of the focal spot and the choice of its size are made at low average power (a watt or less). A frequency sweep is then effected, again at low power, to determine the spectral reflection and resonance characteristics of the crystalline structures variously aggregated within the calculus. In this manner diagnostic information is obtained regarding the nature of the calculus and also information of fundamental importance for choosing the frequencies and form in which to apply the power bursts in order to crumble the crystalline aggregates with minimum energy expenditure.

The aforesaid description relates to the operation of a single focusing/receiving head.

A second head positioned symmetrically opposite the first and in line with the calculus can be likewise used to focus its beam and effect the spectral analysis with a frequency sweep on its energy reflected by the calculus. Each of the two heads can be used for the spectral absorption analysis of the radiation emitted by the other. Thus both the diagnostic information and the information required to define the optimum irradiation program to obtain fragmentation of the calculus are then complete.

We consider that the average and peak powers required for fragmenting the various crystalline aggregates under resonance conditions are only moderate powers, of the average order of some tens of watts and certainly orders of magnitude less than the powers required to crumble the stone substances under pure brute mechanical rupturing action.

Finally, if the observations made on certain calculi which after some months of preservation in a vial easily crumbled at touch into their individual crystals having the size of sand grains (due to the evaporation of their water of hydration) are common to most or to a large proportion of calculi, then their fragmentation would require irradiation with bursts of much lower frequency (corresponding to the much weaker hydration bond) and of energy less by some orders of magnitude than for crystallization.

On this assumption, the ultrasonic system would prove extremely effective and of moderate cost, so making it of widespread use.

A preferred embodiment of the present invention is described hereinafter in greater detail by way of non-limiting example with reference to the accompanying drawings in which:

FIG. 1 shows the equivalence between a monocrystal generator and a resonant electronic network;

FIG. 2A-B shows the relationship between amplitude and phase in a typical resonant circuit;

FIG. 6 shows amplitude/frequency diagrams illustrating the operation of the apparatus of FIG. 5.

Figure 1:
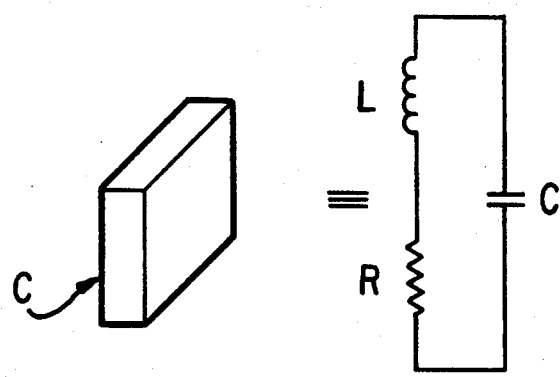
Figure 2A:
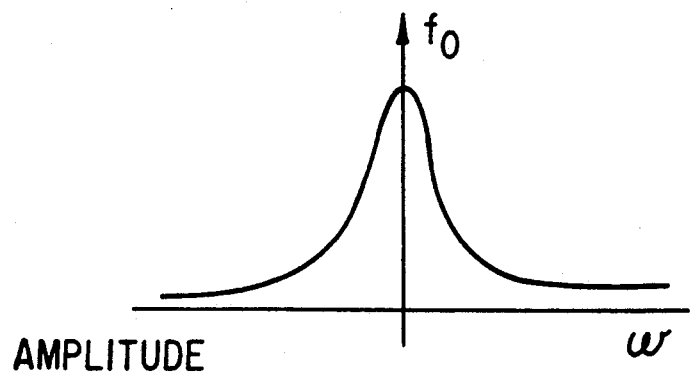
Figure 2B:
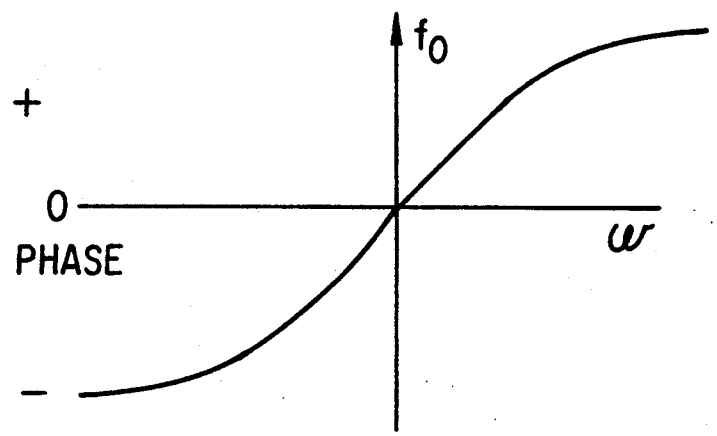
Figure 3:
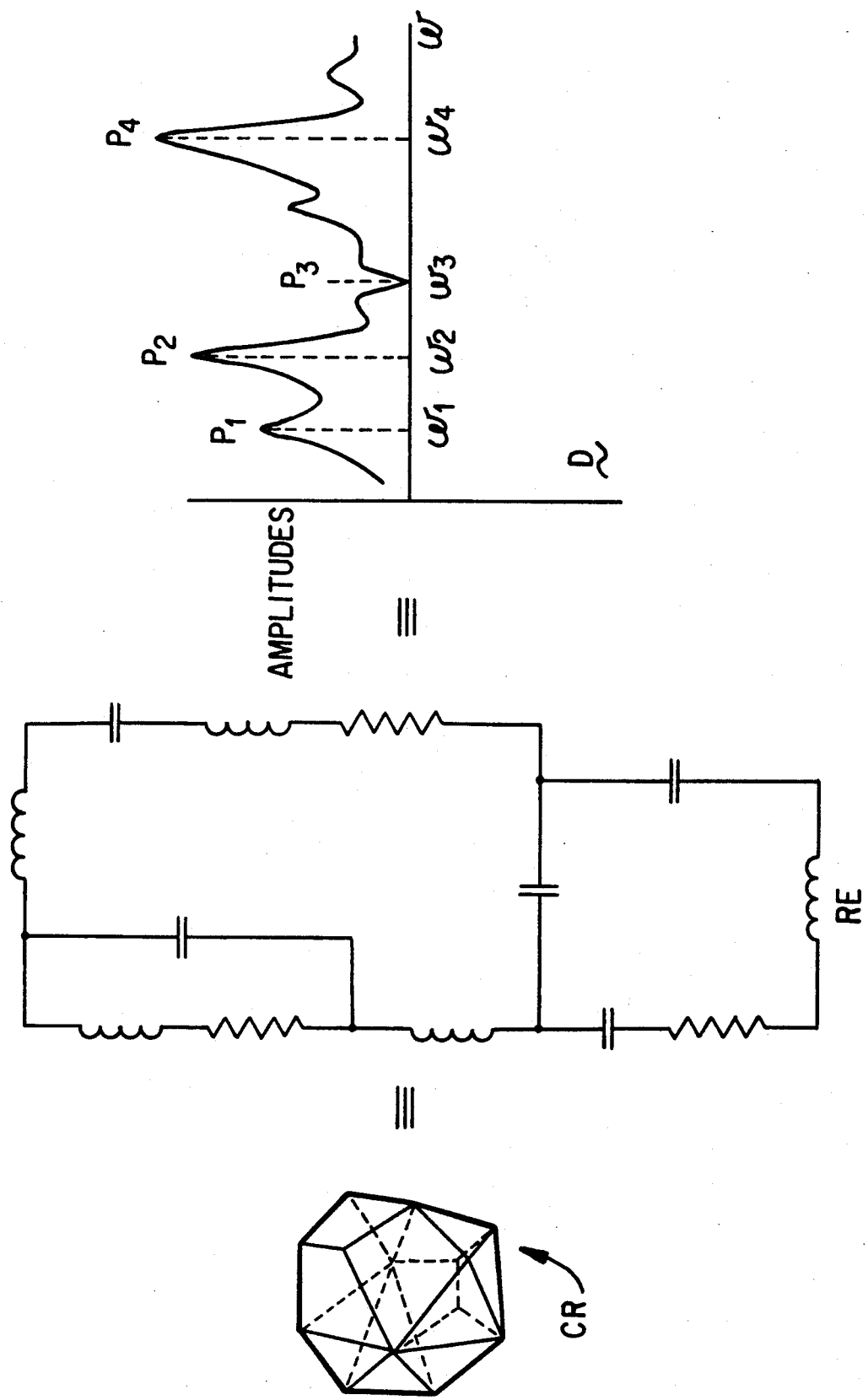
FIG. 3 shows by way of example a polycrystalline concretion structure, the equivalent electrical network and the corresponding diagram of relative amplitudes.

With particular reference to FIGS. 1 to 4 of the drawings, FIG. 1 shows that a generic monocrystal C, for which only one mode of mechanical oscillation is considered, can be considered equivalent to an RLC network. The parameters L, C depend on the geometrical and molecular structure of the crystal whereas the parameter R depends on its internal friction and is one of the basic parameters in the technology of disintegration of crystalline concretions (renal calculi, gallstones or the like) because it constitutes the parameter which determines the absorption of energy by the crystal, this being a maximum at resonance frequency (FIG. 2), as is known from the theory of electrical and mechanical networks. If a polycrystalline structure is present such as for example an effective renal calculus CR (FIG. 3), this will comprise an assembly of monocrystals variously coupled mechanically together, similar to a complex RE network which in the presence of a sweep of frequency $\omega$ presents a characteristic distribution of resonance and absorption peaks as shown by way of example in the diagram D, with peaks P1, P2, P3, P4 of various amplitudes and signs at specific frequencies $\omega_1$, $\omega_2$, $\omega_3$, $\omega_4$.

Figure 4A:
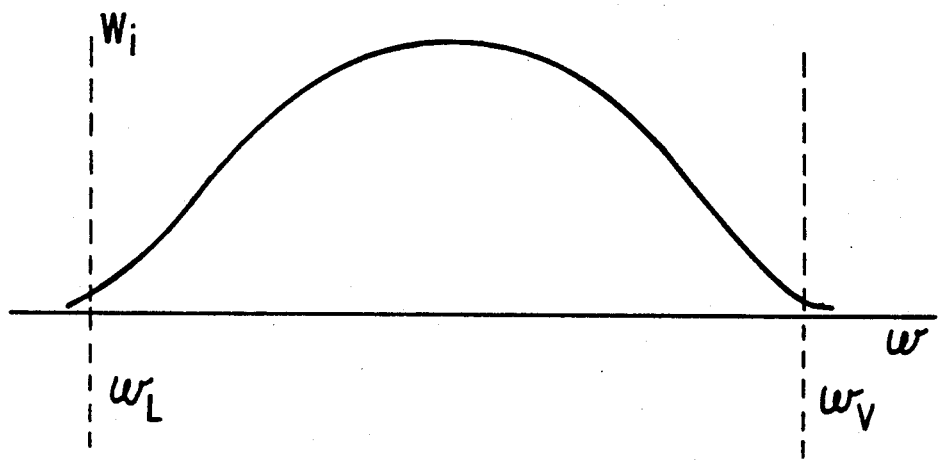
FIGS. 4a and 4b show by way of example the relationship between incident energy and absorbed energy in a generic polycrystalline structure in the prior art.
Figure 4B:
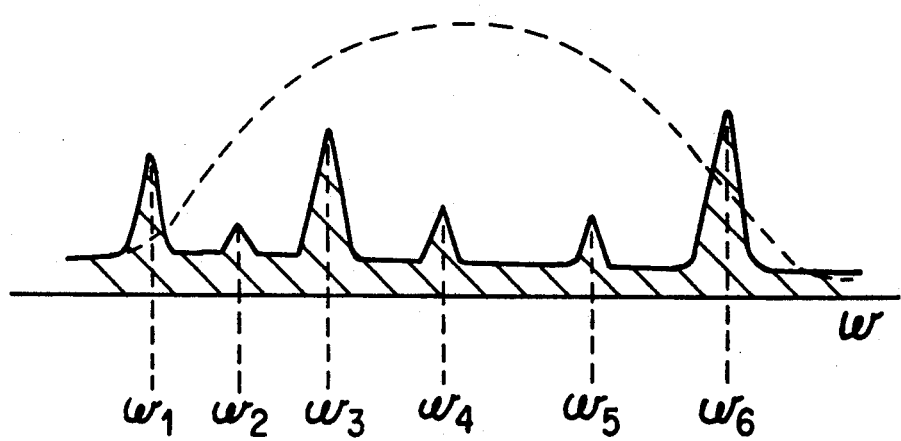

In currently known apparatus for disintegrating renal calculi by shock waves, the incident energy on the consistuent polycrystalline concretion of the renal calculus is distributed over a frequency range shown in FIG. 4a as extending between two limiting frequencies $\omega_L$, $\omega_V$. If the polycrystalline concretion to be demolished has a characteristic frequency spectrum such as that shown schematically in FIG. 4b, at the frequencies $\omega_2$, $\omega_3$, $\omega_4$, $\omega_5$ the energy transfer from the external source to the polycrystalline concretion is acceptable whereas at the frequencies $\omega_1$ and $\omega_6$ is insufficient. Moreover, as the incident power $\omega_i$ is distributed in a substantially uniform manner (wide spectrum shock waves), only that part of the incident energy indicated by the dashed zone is absorbed, while the rest remains unused or can indeed damage other structures of the patient's body.

One embodiment of the apparatus according to the present invention is described hereinafter with reference to FIGS. 5 and 6.

The patient's body, indicated overall by the reference numeral 10, is affected for example by a renal calculus 11. The patient's body 10 is immersed in water or another medium suitable for transmitting ultrasonic elastic waves together with the focusing heads indicated overall by 12 and 13. Each head 12, 13 comprises ultrasonic wave focusing means represented by a parabolic reflector 14, 15, each positioned to cooperate with a transmission transducer 16, 17 and a reception transducer 18, 19.

The transmission transducers are controlled by power amplifiers indicated respectively by Tx1, Tx2, which are excited by variable frequency oscillators OSC1, OSC2.

Control terminals a1, a2 on the transmitters Tx1, Tx2 enable a computer CPU to vary the radiated power level to the calculus 11, and terminals sf1, sf2 enable the computer CPU to control the frequency of the oscillation produced by the two variable frequency oscillators OSC1, OSC2.

The computer CPU is associated with peripherals of known type such as a control keyboard KB, a memory unit MEM and a video display unit M.

The heads 12, 13 comprise reception transducers 18, 19 associated with amplifiers Rx1, Rx2 connected to the computer CPU to provide this latter with information regarding reflected energy, transmitted energy and energy absorbed by the renal calculus 11.

The detailed structure of the transmitters Tx1, Tx2 or receivers Rx1, Rx2 is not described herein as it forms part of the current art known to an expert in the sonar, echography, non-destructive ultrasonic analysis and other fields.

The operating procedure is as follows.

A spectral analysis is firstly carried out on the highest susceptibility peaks of the calculus structure at the various available ultrasonic frequencies by means of a low-power sweep, to obtain a spectrogram of the type shown in FIG. 6A, in which the peaks P1, P2, P3, P4, P5, P6, P7 can be noted.

By means of the head 12 or 13, or both heads, power peaks able to disintegrate the calculus structure are then selectively emitted (FIG. 6B) and a new spectral analysis is effected, shown in FIG. 6C in which it can be seen that the peaks P3, P5, P6 and P7 still remain, whereas the other have disappeared to confirm the disintegration of those parts of the structure associated with these peaks.

New power peaks are then emitted as indicated in FIG. 6D, possibly at greater power than used during the stage represented by FIG. 6B. After this a spectral analysis is again made (FIG. 6E) from which it can be seen that the peaks P1–P7 have all disappeared but that new peaks P8, P9 have appeared. Two new power peaks are then emitted as shown in FIG. 6F. A further spectral analysis (FIG. 6G) shows a "flat" curve indicating that there are no further solid structures detectable by ultrasonic means within the frequency band of the original crystalline concretion, and that the renal calculus 11 has therefore been totally disintegrated.

Figure 5:
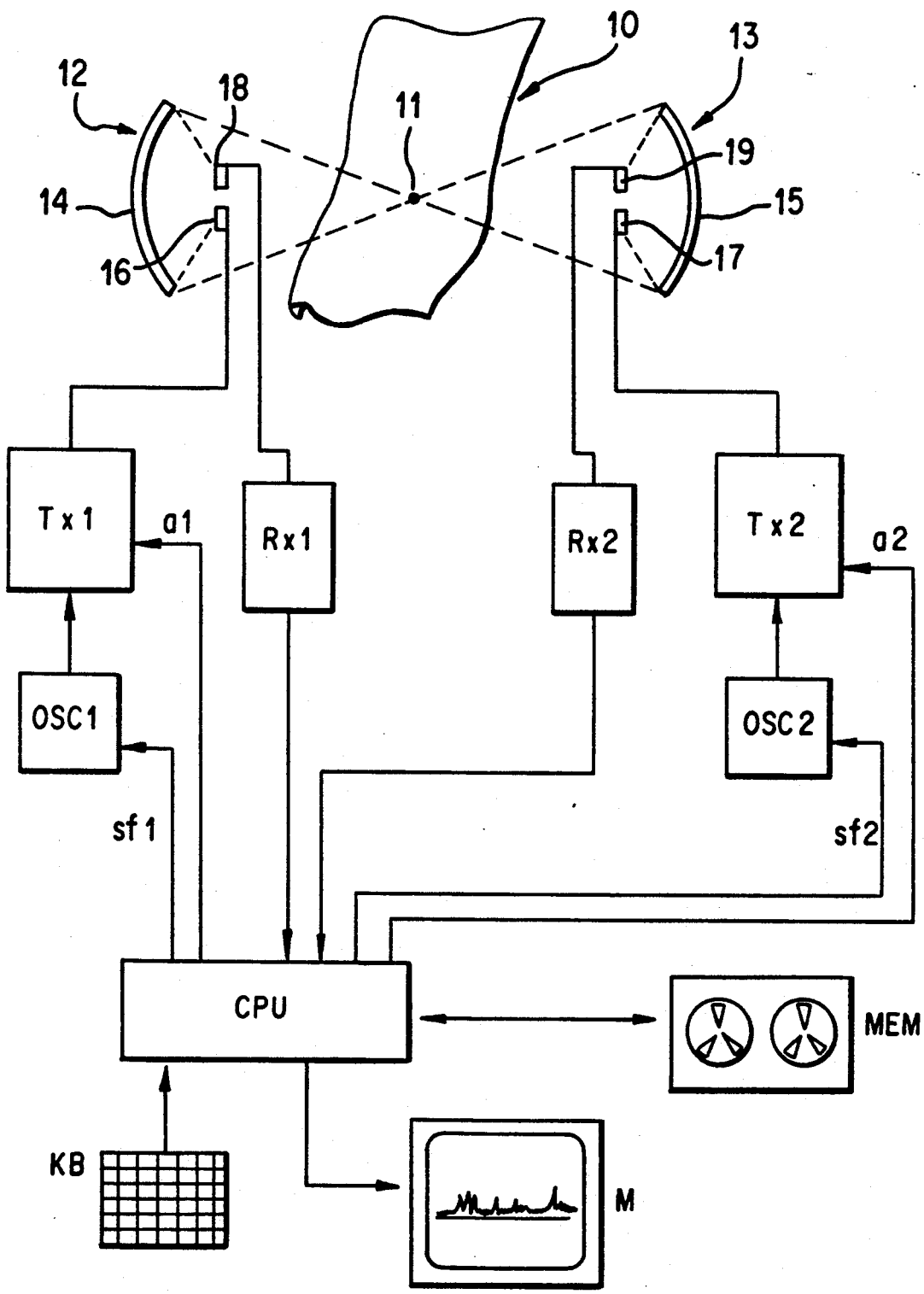
FIG. 5 is a diagrammatic illustration of one embodiment of the apparatus according to the present invention.

It should be noted that in the aforegoing description relative to FIGS. 5 and 6 reference has been made to "amplitude" in the spectral analyses. It will be obvious to the expert of the art that this is a non-limiting example in that the spectral analysis can include consideration of the phase of the signal received by the reception transducers, and/or possible Doppler components as is well known from echographic techniques and from ultrasonic diagnostics carried out in the medical or structural analysis fields, and thus give fullest possible utilisation of the apparatus according to the invention, which as stated is based on spectrally pure ultrasonic emissions rather than semicontinuous or in any event uncontrolled spectral emissions as in the case of the shock waves of the known art.

It should also be noted that in FIG. 5 the heads 12, 13 are shown comprising parabolic reflectors 14, 15. It is however apparent that, in place of or in association with these, structures of lens and focusing wave guide type can be used.

Instead of a structure with single reception-transmission transducers and transmitters and receivers, it is also conveniently possible to use a phased array structure well known in advanced radar and sonar techniques (synthetic-aperture antenna), with the advantage that the focusing, emission and reception structures can be completely static and controlled by a suitable computer, thus considerably simplifying the analysis and intervention operations.

Finally, the receiver-transmitter head phases can be adjustable in order to obtain, in accordance with acoustic holography technology, further diagnostic information (such as shape, thickness, structure etc.) relative to the calculi and to further improve the disintegration action as thickness decreases, and more generally as the shape and constitution of the calculus vary during its breakdown.

The above description has been made with reference to a renal calculus just by way of example. It is obvious that other similar polycrystalline structures such as gallstone or the like can be disintegrated by means of the apparatus according to the invention.

It is apparent that many variations can be made to the apparatus of the present invention, but without leaving its scope of protection.

I claim:

1. An apparatus for the non-intrusive fragmentation of a renal calculus to be disintegrated by ultrasonic oscillations which are focussed on the renal calculus to be disintegrated, said apparatus comprising:

at least one receiver-transmitter head means for receiving and transmitting ultrasonic waves which are focussed on the renal calculus to be disintegrated, each said at least one receiver-transmitter head means including variable frequency transmitting means for generating ultrasonic oscillations having wavelengths within a very narrow band and receiver means for receiving ultrasonic waves reflected from the renal calculus to be disintegrated;

control means for effecting a frequency sweep of ultrasonic waves at low power over the renal calculus to be disintegrated;

means connected to said receiver means for performing a spectral analysis of the characteristic resonance frequencies corresponding to various crystalline structures aggregated within the renal calculus to be disintegrated based on said frequency sweep at low power, whereupon said transmitting means is caused to emit energy bursts of relatively high-power energy pulses possessing the minimum energy at the characteristic resonance frequencies of the renal calculus to effect its disintegration, wherein further low power frequency sweeps can be effected to determine the characteristic resonance frequencies of any remaining crystalline structures within the renal calculus so that the high-power energy pulses can be adjusted depending on the shape and constitution of the renal calculus during its disintegration.

2. An apparatus as in claim 1, wherein two of said receiver-transmitter head means are used, said head means being disposed in a line substantially symmetrically about the renal calculus to be disintegrated.

3. An apparatus as in claim 1, wherein said means for performing a spectral analysis includes a computer and data processing means associated with said at least one receiver-transmitter head means, said computing and data processing means including a data presentation unit and a memory unit, said computing and data processing means performing repetition and comparison on the characteristics of the renal calculus to be disintegrated and said computing and data processing means selecting, setting and controlling the parameters of the high-power energy pulses to further facilitate the disintegration of the renal calculus.

4. An apparatus as in claim 3, wherein said computing and data processing means selects, sets and controls parameters including amplitude, shape, duration, and number of pulses forming a sequence or train, the time interval separating the pulses within a train related to pulse duration, and variation in frequencies and phases of the pulses while the burst progresses and between bursts.

5. An apparatus as in claim 1, wherein said receiver-transmitter head means includes a parabolic reflector as an ultrasonic energy focussing means.

* * * * *